(12) United States Patent
Pedersen-Bjergaard et al.

(10) Patent No.: US 7,445,939 B2
(45) Date of Patent: Nov. 4, 2008

(54) STABLE LIQUID MEMBRANES FOR LIQUID PHASE MICROEXTRACTION

(75) Inventors: Stig Pedersen-Bjergaard, Oslo (NO); Knut Rasmussen, Eiksmarka (NO)

(73) Assignee: Varian, Inc., Palo Alto, CA (US)

( * ) Notice: Subject to any disclaimer, the term of this patent is extended or adjusted under 35 U.S.C. 154(b) by 771 days.

(21) Appl. No.: 10/788,592

(22) Filed: Feb. 27, 2004

(65) Prior Publication Data

US 2005/0191759 A1  Sep. 1, 2005

(51) Int. Cl.
*G01N 1/34* (2006.01)
*G01N 1/40* (2006.01)
*B01D 61/18* (2006.01)
*B01D 61/28* (2006.01)
*B01D 63/02* (2006.01)

(52) U.S. Cl. .................. 436/178; 436/177; 422/101

(58) Field of Classification Search ................. 436/178; 210/635, 490, 639, 644; 516/29; 424/473; 95/54
See application file for complete search history.

(56) References Cited

U.S. PATENT DOCUMENTS

| | | | | |
|---|---|---|---|---|
| 3,959,173 A | * | 5/1976 | Li et al. | 516/29 |
| 4,900,334 A | * | 2/1990 | Admassu et al. | 95/54 |
| 5,160,627 A | * | 11/1992 | Cussler et al. | 210/639 |
| 5,507,949 A | * | 4/1996 | Ho | 210/490 |
| 5,603,953 A | * | 2/1997 | Herbig et al. | 424/473 |
| 5,637,224 A | * | 6/1997 | Sirkar et al. | 210/644 |
| 5,861,097 A | * | 1/1999 | Schafer et al. | 210/635 |
| 6,354,443 B1 | * | 3/2002 | Moya | 210/490 |
| 2004/0171169 A1 | * | 9/2004 | Kallury et al. | 436/178 |

FOREIGN PATENT DOCUMENTS

WO  WO 00/33050  6/2000
WO  WO 02/088672  11/2002

OTHER PUBLICATIONS

Jonsson, Jan Ake, et al. Membrane extraction in analytical chemistry. Jul. 24, 2001. J Sep Sci, 24, 495-507.*
Macasek F. et al, Emulsion Membrane Systems for Preconcentration of Uranium,1985, J. Radioanal. Nucl. Chem., Letters 96/5/529-538.*

* cited by examiner

*Primary Examiner*—Walter D. Griffin
*Assistant Examiner*—Christine T Mui
(74) *Attorney, Agent, or Firm*—Bella Fishman; Cynthia R. Moore

(57) ABSTRACT

The invention provides devices and methods for performing liquid phase microextraction of at least one analyte from an aqueous sample, wherein the device comprises a liquid membrane comprising a fatty acid ester, a vegetable oil, a silicone oil, a nitroarylalkylether, or mixtures thereof, and an optional carrier, supported on a porous polymeric substrate. In a preferred embodiment, the porous polymeric substrate is a hollow fiber. The devices and methods for preparing them provide stable liquid membranes for performing liquid phase microextraction, where the membranes can be stored for 30, 60 or 90 days prior to use.

30 Claims, 5 Drawing Sheets

STABLE LIQUID MEMBRANES FOR LIQUID PHASE MICROEXTRACTION

FIELD OF THE INVENTION

This invention relates generally to sample preparation techniques comprising extraction of analytes from a crude sample using microextraction devices and methods.

BACKGROUND OF THE INVENTION

Sample pretreatment is often a desired preliminary step prior to analysis of complex samples of biological origin. Analytes can be present at insufficient concentration, precluding detection or requiring application of excessive sample volumes to the analytical instrument. For example, in separation methods such as gas chromatography (GC), capillary electrophoresis (CE), capillary electrochromatography (CEC) and high performance liquid chromatography (HPLC), sample volumes are in the range of nL to μL, requiring that analytes be present in amounts sufficient for detection in those volumes. In addition, contaminants such as salts, metals, buffers, proteins, etc. can be present in complex samples and could interfere with or damage sensitive instruments. Therefore, pretreatment of samples is usually necessary prior to analysis of the samples.

Sample preparation is the most time consuming step in the analysis of drugs or other active agents present in the concentration range of pg/mL to μg/mL in biological samples such as serum, urine, blood, water samples, etc. Sample preparation procedures are needed that are fast and simple to perform, provide good recovery of analytes from interfering contaminants, and concentrate analytes so that sufficient quantities of analytes are present in the desired volume for analysis. Ideally, the sample preparation step is able to trap analytes in 1-50 μL of solvent that can be directly injected into the analytical instrument. For example, for GC, it is preferred that the analytes are concentrated into an organic solvent that can be introduced into the gas chromatograph, while for CE or HPLC, aqueous solvents are preferred.

The most frequently used extraction techniques are liquid-liquid extraction (LLE) and solid-phase extraction (SPE), resulting in concentration of analytes into solvent volumes of 0.2 to 10 mL of extraction solvent based on partitioning of analytes into the acceptor phase. However, for small sample volumes, these techniques result in poor recovery of analytes and/or analyte concentrations that are too low for analysis. As discussed in WO 00/33050, quantitative extraction using LLE can only be achieved by using large volumes of extraction solvent relative to the sample volume. Generally a volume of solvent of from one half to ten times the volume of the sample is used, which results in a need for an additional concentration step, and further increases the time involved in sample preparation and reduces analyte recovery. Using SPE, 100 mg of adsorbent is generally required to extract analytes from a 1 mL sample, and results in a maximum concentration enhancement of a factor of 4, assuming quantitative recovery from the solid phase adsorbent. It is desired to purify and concentrate analytes in a solvent by a factor of 10 to 100 or more, which is not possible using LLE or SPE.

Microextraction procedures provide one partial solution to these problems. In microextraction procedures, the analytes are extracted from a large volume of sample into a smaller volume of an acceptor phase. The acceptor phase can be a solid phase, as in solid-phase microextraction (SPME), an organic solvent as in liquid-liquid microextraction (LLME) or an aqueous solvent as in liquid-liquid-liquid microextraction (LLLME) also known as liquid phase microextraction (LPME), wherein uncharged analytes are first equilibrated with an intermediate organic phase, then trapped in an aqueous acceptor phase in a charged and impermeable form which cannot traverse across the organic phase back to the sample solution.

Adsorption onto the solid phase in SPME is accomplished using a solid polymer coated onto a fiber. The polymer acceptor phase is nonvolatile and has a volume less than 1 μL. However, when applied to trace analysis of organic compounds from complex biological samples, enrichment from the biological matrix is reduced relative to enrichment from a water sample, due to the reduced capacity of the acceptor phase.

Liquid phase microextraction (LPME) encompasses both LLME and LLLME, and overcomes many of the limitations of solid phase extraction and microextraction. For example, as shown in FIG. 1 of WO 00/33050, extraction of an analyte from a sample containing 1 μg/mL of the analyte results in a concentration at equilibrium of 0.99 μg/mL in the acceptor phase using LLE and a concentration of 50 μg/mL in the acceptor phase using LLME, when the partition coefficient between the aqueous phase and the acceptor phase is 100. As demonstrated in Table 1 of WO 00/33050, enrichment of analyte in the acceptor phase depends on the volume of the acceptor phase and the partition coefficient. Enrichments of from about 1 to 500 are possible from a sample containing 1 μg/mL of analyte into acceptor phases with partition coefficients of 10 to 1000, respectively.

It is desirable to keep the acceptor phase separate from the sample in order to facilitate recovery of the acceptor solution and the enriched analytes. The acceptor phase can be maintained separate from the donor or sample phase by, for example, incorporating the acceptor phase into sponges, from which it can be removed after extraction is complete, by filling a hollow fiber of porous polymer with the acceptor phase, from which it can be withdrawn after extraction is complete, or by forming a liquid membrane on the surface of a hollow fiber of porous polymer where the ultimate acceptor phase is aqueous and is present on the interior of the hollow fiber. The aqueous acceptor phase enriched in analytes can then be removed after extraction is complete. The first two approaches (LLME) allow the enrichment of the analyte directly into the acceptor phase. The latter approach (LLLME) also allows the selective enrichment of acidic and basic compounds. For example, enrichment of a carboxylic acid analyte is effected from a sample by adjusting the pH of the sample solution below the pKa of the acid so that the carboxylic acid is neutralized and partitions into the liquid membrane, while the pH of the acceptor aqueous solution is above the pKa of the acid, causing the analyte diffusing into the acceptor solution to be trapped in its charged form. The principles of LLLME and LLME are discussed in detail in WO 00/33050.

WO 02/088672 discloses supported liquid membranes, for example, porous membrane supports, which are impregnated with a water insoluble organic solvent, for performing LLLME. Porous hollow fiber or porous-disk liquid membrane devices and methods of use are described that allow purification and enrichment by factors of several hundred for analytes of interest from biological fluid samples. However, for this technique to work optimally, stable membranes are required which are also permeable to analytes of varying hydrophobicity. The devices and methods described in WO 02/088672 are reported to utilize solvents that are immiscible with water as liquid membranes, including aliphatic or aromatic hydrocarbons, ethers, nitrites, aldehydes or ketones, and alcohols. This reference reports that the most stable membranes were formed when using hydrophobic liquids, such as pure hydrocarbons (e.g., dodecane), while the greatest diffusion and hence optimal analyte enrichment occurred when utilizing more polar solvents. A balance between stability and analyte diffusion was sought by mixing the solvents to achieve stable liquid membranes with high diffusion coefficients to analytes. However, WO 02/088672 also discloses that, once prepared, these supported liquid membranes generally have limited lifetimes. One solvent, nitrophenyloctylether, was reported to provide a membrane lifetime of 10-20 days, while the others tested possessed lifetimes of at most 5 days.

Therefore, there is a need in the art for more stable and permeable liquid membrane devices for performing LPME. There is also a need in the art for improved methods of preparing and using these devices in the performance of LPME.

SUMMARY OF THE INVENTION

Accordingly, it is a primary object of the invention to address the aforementioned need in the art by providing improved methods and devices for preparing samples for analysis. It is a further object to provide more stable liquid membranes for use in conducting LPME. It is yet a further object to provide improved methods of preparing and using supported liquid membranes for conducting LPME.

Accordingly, the present invention involves the discovery of improved methods and devices providing for preparation and storage of liquid membranes useful in LPME. Using these discoveries, liquid membranes can be prepared that exhibit stable extraction performance for at least 30, 60 or 90 days.

Accordingly, the invention provides a device for performing liquid phase microextraction of at least one analyte from an aqueous sample comprising a liquid membrane supported on a porous polymeric substrate. The liquid membrane has one side that can be placed in fluid communication with the aqueous sample containing the at least one analyte and a second side that can be placed in fluid communication with an acceptor solution. In a preferred embodiment, the porous polymeric substrate is a hollow fiber, and in operation, the acceptor solution is contained within the hollow fiber and the device is inserted into the sample solution to perform the extraction. The acceptor solution can be any suitable aqueous medium containing salts, buffers, etc. as known in the art. The composition of the acceptor solution is chosen so that the acceptor solution is capable of accepting at least one analyte from the sample.

The liquid membrane comprises a fatty acid ester, a vegetable oil, a silicone oil, a nitroarylalkylether, or mixtures of these components. The fatty acid ester comprises an acyl chain comprising from 12 to 30 carbon atoms, and an ester portion comprising from 1 to 12 carbon atoms. The acyl chain or the ester portion comprising from 1 to 12 carbons can be a branched or unbranched carbon chain. The liquid membrane can also comprise a vegetable oil such as soya oil, olive oil or tea tree oil, or a nitroarylalkylether, or mixtures thereof. Preferably the alkyl portion of the nitroarylalkylether comprises from 5 to 30 carbons, and the aryl portion of the nitroarylalkylether comprises from 5 to 20 carbons. The aryl moiety can also be optionally be substituted with 1-4 substituents selected from hydroxyl, nitro, and $C_1$-$C_6$ hydrocarbyl.

The liquid membrane can also comprise a carrier. The carrier is typically an organic ion, an ionophore or a pore forming agent. Preferred carriers are organic ions, examples of which include trioctylphosphine oxide (TOPO), diethylhexyl phosphoric acid, triethylhexyl phosphoric acid, dodecylbenzene sulphonic acid, aliquat 336 (trioctylmethylammonium chloride), amberlite LA, tri-n-octyl amine, tetraphenylphosphonium, tetraphenylarsonium, trinitrophenol, and tetraphenylboron.

The polymeric substrate comprises a polyolefin, acrylic copolymer, polyamide, polyester, polyurethane, polycarbonate, polystyrene, fluorinated polymer, polyvinyl chloride, polyacrylonitrile, copolymers thereof, or mixtures thereof. Preferably, the polymeric substrate comprises a polyolefin, such as polyethylene, polypropylene, polytetrafluoroethylene, poly(tetrafluoroethylene-co-ethylene), or polyethylene-polyvinyl chloride copolymer, copolymers thereof, or mixtures thereof.

The liquid membrane is stable and can be stored until the end user is ready to perform an extraction. Generally, the liquid membrane is stable for at least 30 days, 60 days, or 90 days. In a preferred embodiment, the liquid membrane is formed on a porous hollow fiber. Preferably, the liquid membrane formed or coated onto the hollow fiber is able to extract at least one analyte after being stored for at least 30 days. More preferably, the hollow fiber is able to extract at least one analyte after being stored for at least 60 days, or even 90 days. Preferably, the liquid membrane formed on the hollow fiber is stored at a temperature at or below 40° C., or more preferably at room temperature. The liquid membrane is stored in a closed container.

In operation of a preferred embodiment, the acceptor solution is placed inside the hollow fiber and the hollow fiber is placed in the sample solution. The acceptor solution can be withdrawn from the hollow fiber manually using a syringe, or the acceptor solution can be sampled by an autosampler.

In other embodiments, the device is in a form that places the liquid membrane between two chambers for containing solutions, such as between the sample solution and the acceptor solution, for example, by forming the liquid membrane on a porous polymeric substrate in the form of a sheet or disk In another embodiment, the invention provides a method for performing liquid phase microextraction of at least one analyte from a sample solution, comprising contacting the sample solution containing the at least one analyte with one side of a liquid membrane having two sides formed on a porous polymeric substrate, and contacting an acceptor solution with a second side of the liquid membrane. The extraction can be continued for a time sufficient to allow transfer of the analyte to the acceptor solution, generally 15-60 minutes. However, the time for performing the extraction can be increased or decreased depending, for example, on the concentration of the analyte in the sample solution, the detection limits of the assay procedure used to detect the analyte in the acceptor solution, the liquid membrane composition, the partition coefficient of the analyte into the liquid membrane, the temperature at which the extraction is performed, and the composition of the sample and acceptor solutions. The sample solution, the acceptor solution, or both solutions can be agitated, such as by stirring by magnetic or mechanical means.

Generally, the sample solution is a biological sample or an environmental sample. Alternatively, the sample can be prepared from a dispersion of any solid matter in aqueous solution, including soil, food, plant matter, animal tissues, fungal or bacterial matter, waste materials, or aqueous samples of dissolved airborne compounds. Preferably, the biological sample is urine, plasma, blood, lymph, cerebrospinal fluid, tears, sweat, mucous secretions (e.g., saliva, vaginal secretions, etc.), gastrointestinal fluids, or cell culture fluid. The environmental sample is preferably condensed water, surface water, ground water, rain water, river water, sea water, lake water, effluent water, influent water, or drinking water.

In another preferred embodiment, the porous polymer substrate is a hollow fiber, and the acceptor solution is contained within the hollow fiber. The sample solution can be contacted with the liquid membrane by placing the hollow fiber in the sample solution. Preferably, the hollow fiber is able to extract at least one analyte after being stored at room temperature for 30 days, more preferably 60 days, and even 90 days.

In another embodiment, a method is provided for preparing a liquid membrane on a porous polymeric substrate for performing liquid phase microextraction, comprising the step of applying an organic phase comprising a fatty acid ester, a vegetable oil, a silicone oil, a nitroarylalkylether, or mixtures thereof to a porous polymeric substrate to form a liquid membrane on said porous polymeric substrate. In a certain embodiments, the porous polymeric substrate is in the form of a hollow fiber or a sheet. The method can further comprise removing excess organic phase, such as by sonicating or rinsing the porous polymeric substrate. In a preferred embodiment, the porous polymeric substrate is in the form of a hollow fiber. In other preferred embodiments, the porous polymeric substrate is in a substantially planar sheet-like form, such as a disk. The liquid membranes formed on the porous polymeric substrate can then be stored preferably in a covered container in air until use.

Additional objects, advantages and novel features of the invention will be set forth in part in the description which follows, and in part will become apparent to those skilled in the art upon examination of the following, or may be learned by practice of the invention.

DETAILED DESCRIPTION OF THE INVENTION

I. Definitions and Overview

Before the present invention is described in detail, it is to be understood that unless otherwise indicated this invention is not limited to specific organic phases, polymeric substrates, pore sizes, polymer thicknesses, analytes or the like, as such may vary. It is also to be understood that the terminology used herein is for the purpose of describing particular embodiments only and is not intended to limit the scope of the present invention.

It must be noted that as used herein and in the claims, the singular forms "a," "and" and "the" include plural referents unless the context clearly dictates otherwise. Thus, for example, reference to "an analyte" includes two or more analytes; reference to "a polymer" includes two or more polymers, and so forth.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

As used herein, the term "liquid membrane" refers to the thin film of organic phase liquid formed onto porous polymeric substrate. Thus the liquid membrane is "supported" by the polymer substrate. The organic phase fills the pores and coats the surface of the porous polymeric substrate, forming a liquid membrane that in operation separates aqueous phases on either side. A preferred liquid membrane is the liquid membrane formed when hollow fibers are coated with organic phase.

As used herein, the term "stable" refers to the stability of the analyte extraction performance of the liquid membrane used in the LPME device. Generally, a stable liquid membrane remains in place on the porous polymeric substrate with the organic phase filling the pores of the polymeric substrate. An unstable liquid membrane fails to extract analytes due to loss of the organic phase from the surface of the substrate and from the pores. Thus the organic phase of a stable liquid membrane does not evaporate or become absorbed into the polymeric substrate such that it disappears entirely from the polymeric substrate and the pores. In operation, some of the organic phase may mix with the aqueous sample or acceptor phases (as indicated by cloudiness) without loss of stability and extraction ability. Preferably, the analyte extraction performance of the liquid membrane should change by no more than about 15% during appropriate storage, although variation of up to about 30% is generally acceptable. That is, the extraction performance when tested at a later time is within 70-130% or more preferably, within 85-115%, of the value obtained on the day the liquid membrane is prepared. Preferably the liquid membrane is stable for at least 30 days, 60 days, and more preferably at least 90 days of storage.

The term "stored" refers to storage of the liquid membrane in a closed container at a temperature at which the organic liquid is not vaporized, although the container does not have to be airtight. Preferably the temperature for appropriate storage is less than 40° C., and more preferably the storage temperature is room temperature or about 25° C.

II. Devices for Performing Liquid Phase Microextraction

Figure 1:
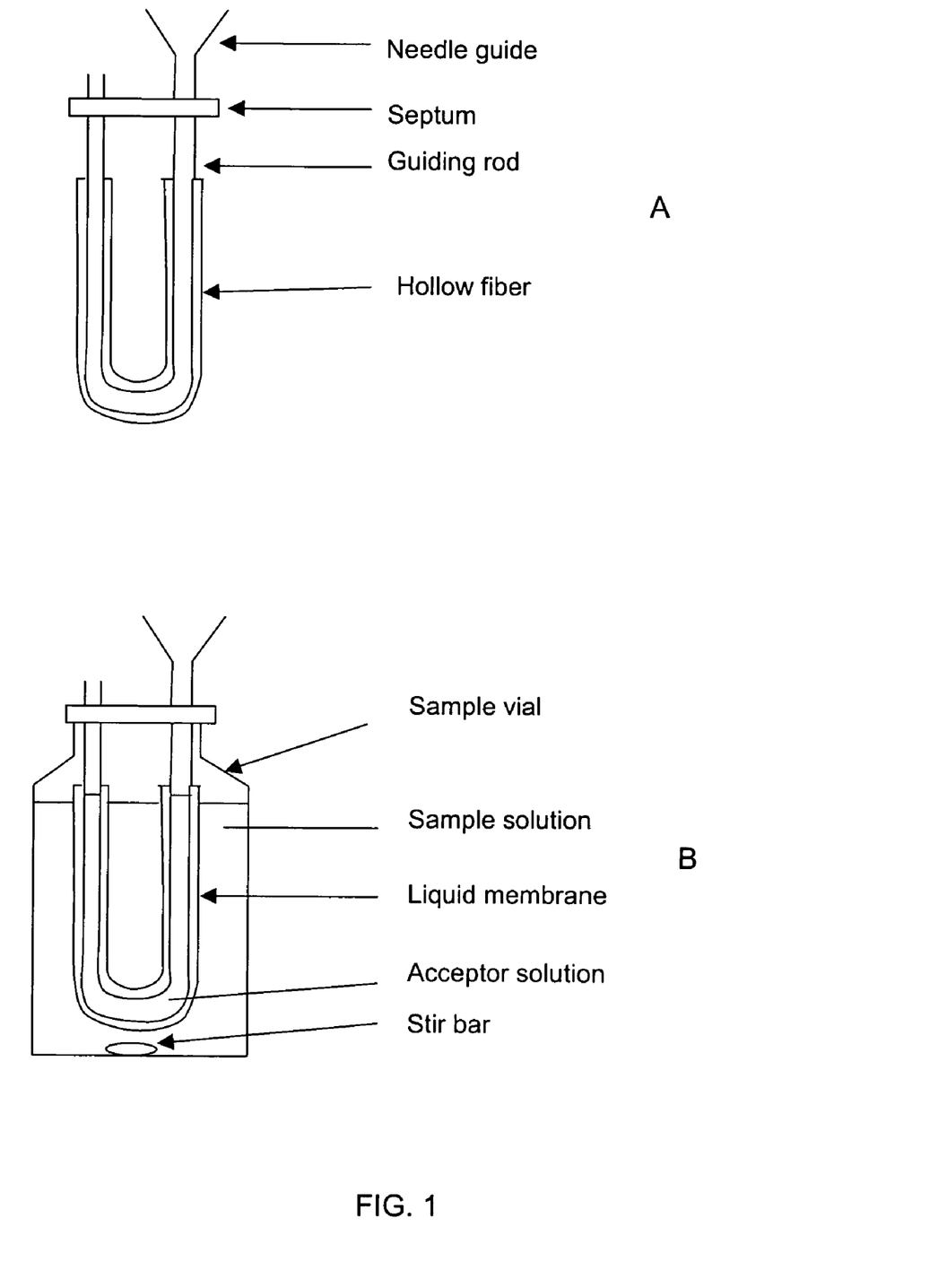
FIG. 1 illustrates a schematic view of a liquid membrane formed on a porous hollow fiber to be used in extraction of analytes from sample vials.
Figure 2:
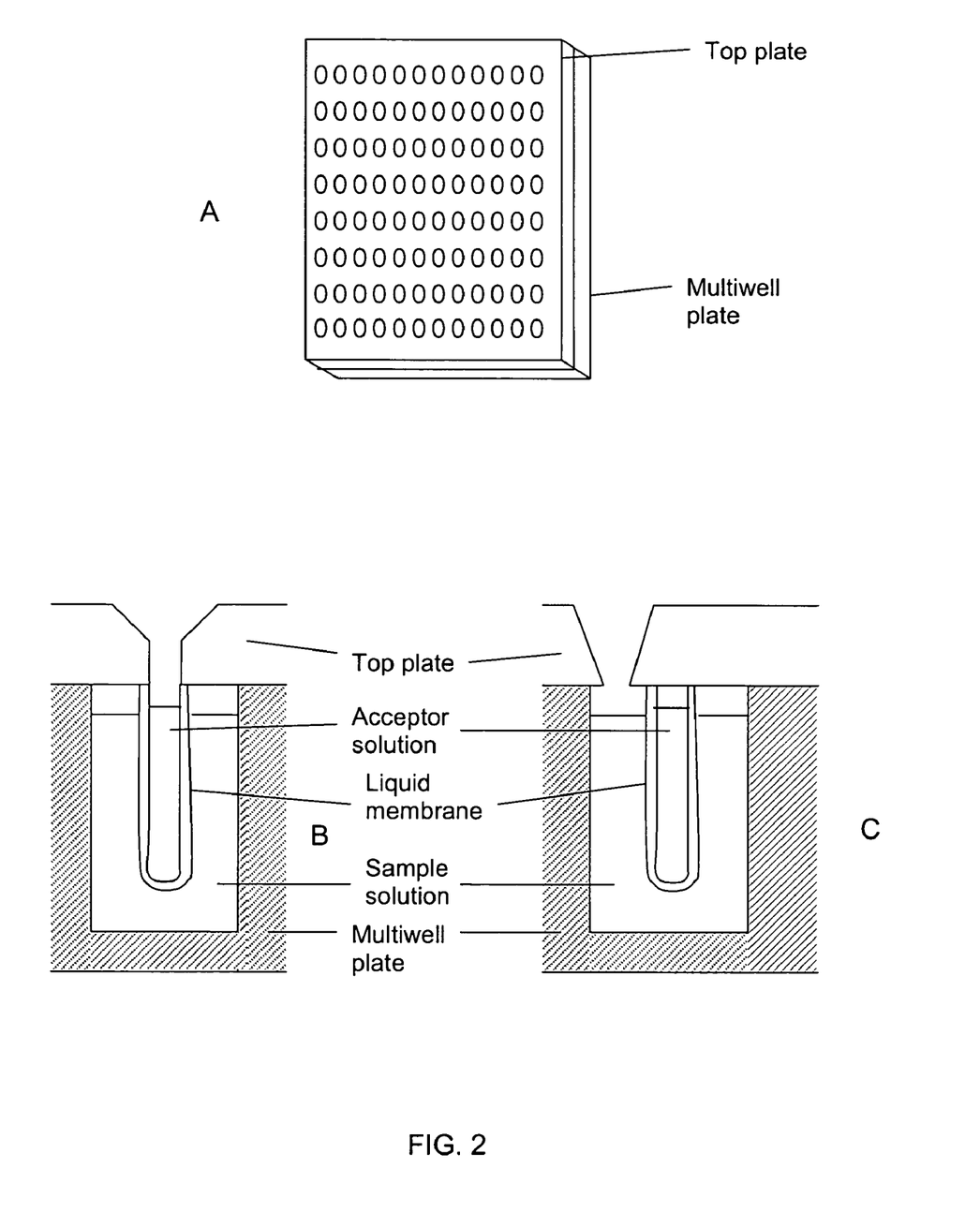
FIG. 2 illustrates an alternative schematic view of a liquid membrane formed on a porous hollow fiber to be used in extraction of analytes contained in a microtiter plate.
Figure 3:
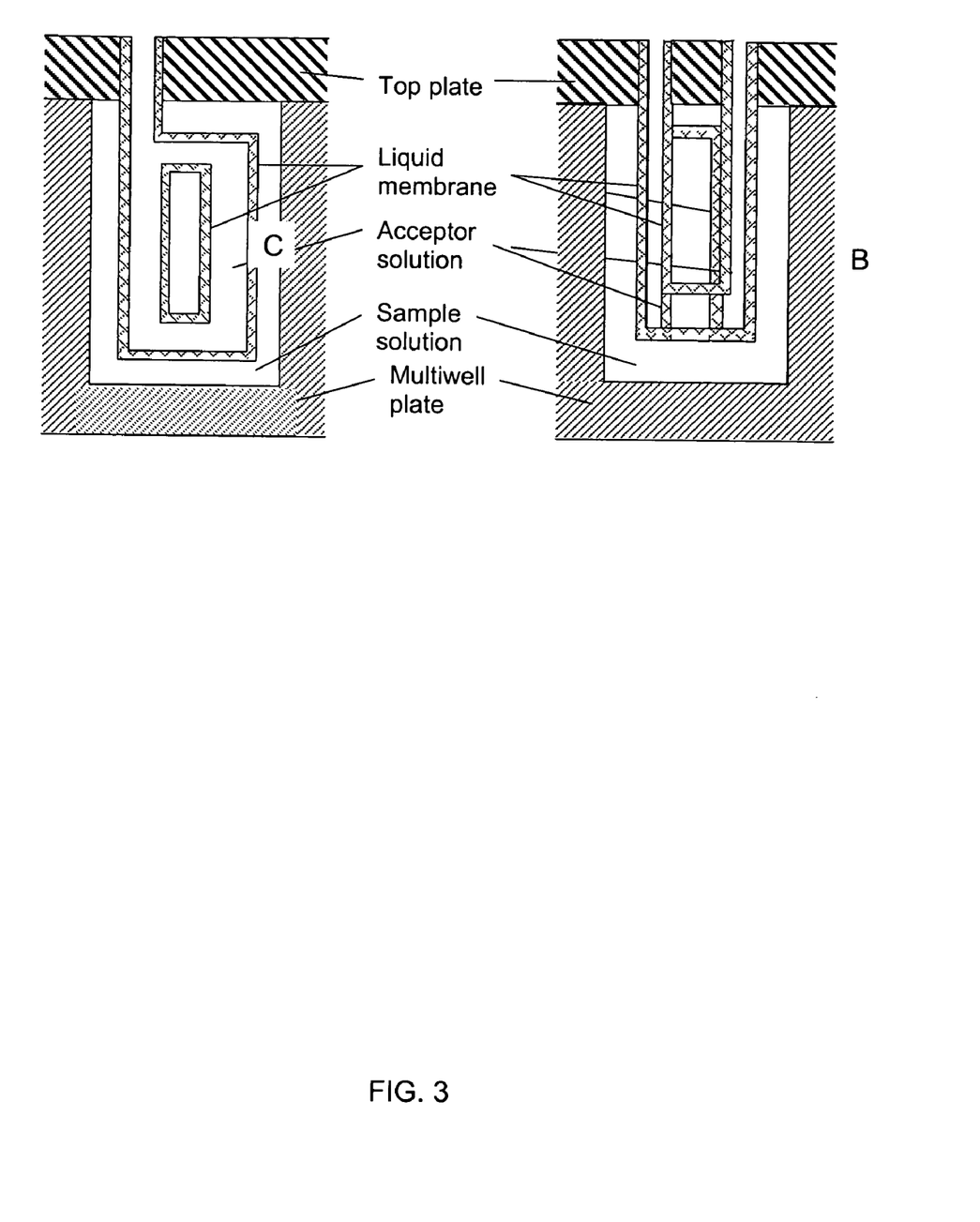
FIG. 3 illustrates three different hollow fiber and sample container geometries in accordance with additional embodiments.

Accordingly, the invention provides a device for performing liquid phase microextraction of at least one analyte from an aqueous sample comprising a liquid membrane supported on a porous polymeric substrate. The liquid membrane has one side that can be placed in fluid communication with the aqueous sample containing the at least one analyte and a second side that can be placed in fluid communication with an acceptor solution. In a preferred embodiment, the porous polymeric substrate is a hollow fiber. Several embodiments of liquid membranes formed on porous hollow fibers are shown in FIGS. 1, 2 and 3. In operation, the acceptor solution can be contained either within the hollow fiber or outside the hollow fiber. Preferably, the acceptor solution is contained within the hollow fiber and the device is inserted into the sample solution to perform the extraction. Alternatively, the sample solution can be placed inside the hollow fiber and the acceptor solution can be placed outside the hollow fiber.

As disclosed herein, devices for performing LPME and methods for preparing liquid membranes provide stable liquid membranes that can be used after extended storage. Previous studies had shown that liquid membranes could be prepared that were generally stable for five days or less, or for as long as 10-20 days had been observed with one particular organic phase. The present work shows surprisingly that liquid membranes can be prepared that are stable for at least 30 days, 60 days, or 90 days of storage.

In a preferred embodiment, the liquid membrane is formed on a porous hollow fiber, and one or several hollow fibers in combination can be used in a single extraction device. Preferably, the liquid membrane formed or coated onto the hollow fiber is able to extract at least one analyte after being stored for at least 30 days. More preferably, the hollow fiber is able to extract at least one analyte after being stored for at least 60 days, or even 90 days. Preferably, the liquid membrane formed on the hollow fiber is stored at a temperature at or below 40° C., or more preferably at room temperature. The liquid membrane is stored in a closed container.

In operation of a preferred embodiment, the acceptor solution is placed inside the hollow fiber and the hollow fiber is placed in the sample solution. The acceptor solution can be withdrawn from the hollow fiber manually using, for example, a syringe or a micropipette, or the acceptor solution can be sampled by an autosampler.

Figure 4:
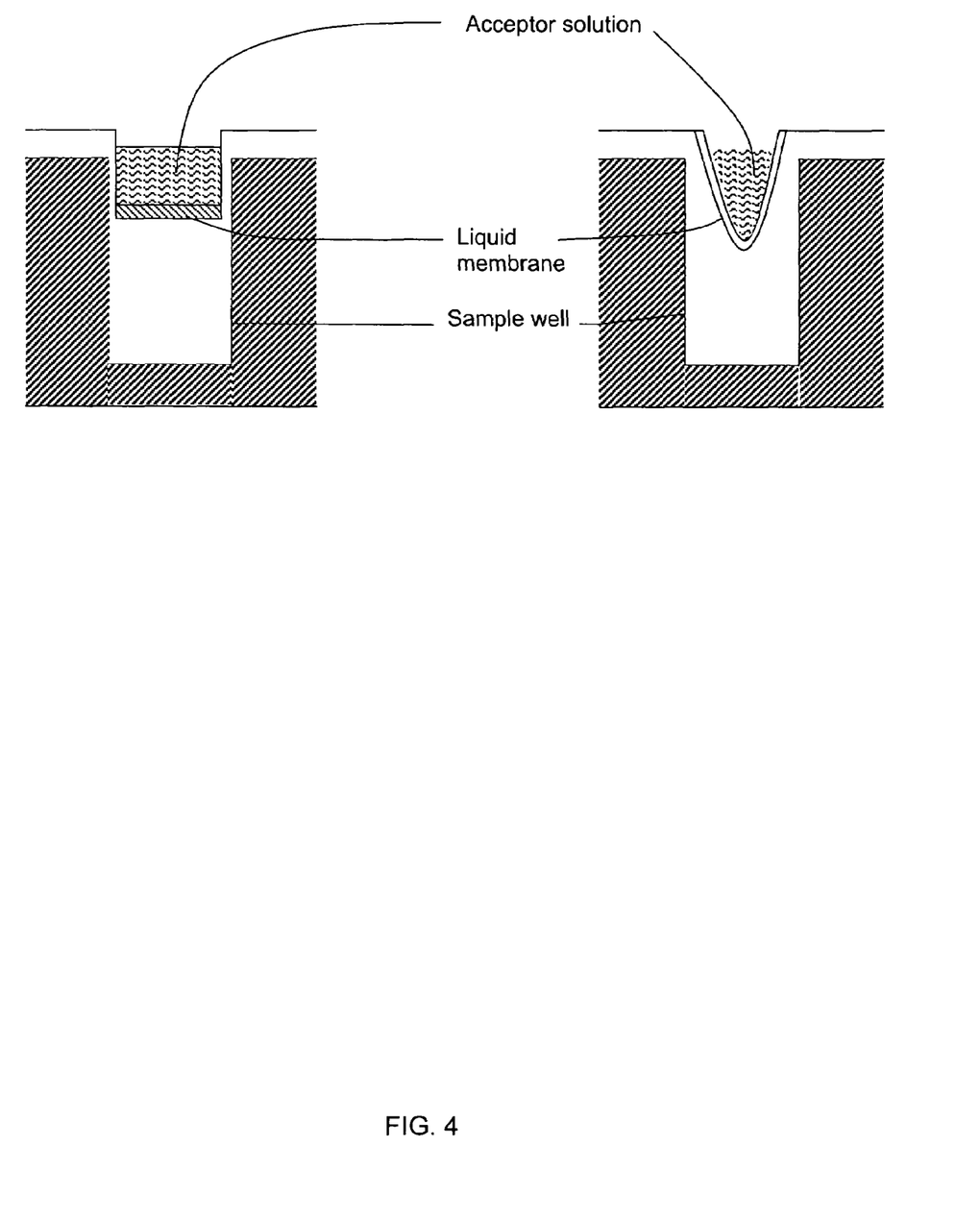
FIG. 4 illustrates a view of a device including a disk-shaped membrane support and a cone shaped membrane support according to additional embodiments.

In other embodiments, the device can be in any form that places the liquid membrane between the sample solution and the acceptor solution, such as by forming the liquid membrane on a porous polymeric substrate in the form of a sheet or disk that can be planar or curved, as shown in FIG. 4.

A. Constituents of Liquid Membranes

1. The Organic Phase

The chemical nature of the liquid membrane is important in obtaining short analysis times. The organic phase which forms the liquid membrane typically possesses sufficient nonpolar character that it does not dissolve into either the sample or acceptor aqueous phases. The analytes of interest in a particular application partition into the organic phase with a partition coefficient of typically more than 50 and preferably greater than 100, providing enrichment of trapped analytes in the acceptor phase between 50 fold and several hundred fold. The boiling point of the organic phase is preferably above 150° C., and the viscosity of the organic phase is preferably low enough to allow rapid diffusion and transport of analytes across the liquid membrane, although a more viscous organic phase can also be used if short extraction times (less than about one hour) are not required. Extractions are generally performed for a sufficient period of time to allow accumulation of analytes in the acceptor solution, but the extraction can also be performed for a sufficient period of time to allow an equilibrium between the three phases to be established. If the membrane/sample partition coefficient is low or the organic phase is very viscous, equilibrium times can be long and can require additional equilibration time. However, it is not necessary to reach equilibrium in order to enrich analytes in the acceptor solution. Therefore it is advantageous that the solvent forming the membrane is a good solvent for the target analyte. The chemical nature of the membrane can also provide selectivity toward particular analytes, and can be tuned for particular applications.

The liquid membrane comprises a fatty acid ester, a vegetable oil, a silicone oil, a nitroarylalkylether, or mixtures of these components, and may optionally contain preservatives such as antioxidants. The fatty acid ester typically comprises an acyl chain comprising from 12 to 30 carbon atoms, and an ester portion comprising from 1 to 12 carbon atoms. The fatty acid esters may be saturated, unsaturated, linear, or branched, and may also include halogenated analogues. Acetate, propionate and butyrate esters are preferred. Exemplary fatty acid esters include, but are not limited to, tributyrin, dodecyl acetate, dodecyl butyrate and myristyl acetate.

Silicone oils (polysiloxanes) can contain functionalities like methyl, phenyl, cyanopropyl, and trifluoropropyl, and mixtures thereof. Exemplary silicone oils include Silicon Oil AR 20 (having a viscosity of about 20 mPascals at 25° C.) and Silicone Oil AS 4 (having a viscosity of about 6 mPascals at 25° C.) (both from Fluka).

Nitroarylalkylethers preferably include an alkyl portion comprising from 5 to 30 carbons, and an aryl portion comprising from 5 to 20 carbons. The aryl moiety can also be optionally be substituted with 1-4 substituents selected from hydroxyl, nitro, and $C_1$-$C_6$ hydrocarbyl. An exemplary nitroarylalkylether is nitrophenyloctyl ether.

Vegetable oils include oil seed oils as well as essential oils, i.e., generally oils obtained by steam distillation of plant matter. Oil seed oils include rapeseed oil, canola oil, soybean oil, corn oil, cottonseed oil, linseed oil, olive oil, tung oil, peanut oil, meadowfoam oil, sunflower oil, safflower oil, jojoba oil, palm oil, castor oil, without limitation. Essential oils include the oils from the Myrtaceae family, including the Australian tea tree (*Melaleuca alternifolia*), manuka (*Leptospermum scoparium*) and kanuka (*Kunzea ericoides*), and oils from aromatic plants such as rosemary, eucalyptus, mint, cinnamon, pine, artemisia, marjoram, peppermint, lavender, citrus or sage, to give a few examples. Soybean oil generally contains a mixture of polyunsaturated fatty acids, mainly $C_{14}$ $C_{16}$, and $C_{18}$, or medium chain triglycerides. Olive oil generally contains mainly mono-unsaturated oleic acid. Tea tree oil generally contains terpene alcohols and cyclic monoterpenes, including 1,8-cineole, 1-terpinen-4-ol, rho-cymene, linalool, alpha-terpinen, gamma-terpinene, alpha-terpineol and terpinolene, among numerous additional minor components. The vegetable oil can be obtained from a genetically modified plant or be modified by water washing, refining, esterification, hydrolysis, hydrogenation, etc. to improve the chemical stability and resistance to oxidation, if desired. Preferably, the vegetable oil is soybean (or soya) oil, olive oil, or tea tree oil.

2. Carriers

The liquid membrane can also comprise a carrier, which can provide selectivity to particular analytes, or can increase the rate at which equilibrium is reached between the sample and acceptor solutions (e.g, by lowering the energy of partition of a water soluble analyte into the organic phase of the liquid membrane). Carriers are typically organic ions, but can also include ionophores and pore forming agents, etc. Examples of organic ions include trioctylphosphine oxide (TOPO), diethylhexyl phosphoric acid, triethylhexyl phosphoric acid, dodecylbenzene sulphonic acid, aliquat 336 (trioctylmethylammonium chloride), amberlite LA, tri-n-octyl amine, tetraphenylphosphonium, tetraphenylarsonium, trinitrophenol, and tetraphenylboron, without limitation. A preferred carrier is TOPO, exemplified in Example 4 below.

Examples of ionophores include valinomycin (e.g., $K^+$, $Cs^+$ transport) and A23187 (e.g., $Ca^{++}$ transport). Pore forming agents include gramicidin and related families of peptides, use of which would allow enrichment of ionic analytes in the acceptor phase. Of course, in the case of ionophores or pore forming agents, which allow otherwise impermeable analytes to cross the liquid membrane and become enriched in the acceptor phase, the analyte may not actually partition into the liquid membrane per se, but instead cross the liquid membrane using the ionophores as a carrier or traverse in an aqueous pore.

Carriers are typically added to the organic phase prior to immobilization on the porous membrane to form the supported liquid membrane, although the carriers can also be added after formation of the liquid membrane. Generally, the addition of the carrier has no affect on the stability of the liquid membranes.

3. Preservatives

Preservatives generally include antioxidants and oxygen scavengers, which act as preservatives by retarding deterioriation of the organic phase due to oxidation. The antioxidants typically are oxygen or free radical scavengers, such as ascorbic acid or salts thereof, erythorbic acid or salts thereof, butylated hydroxytoluene, and the like. The amount of anti-oxidant used is an anti-oxidizing effective amount of the anti-oxidant. Preferably, it is less than 2% by weight, and most preferably it is present in amounts that range from about 0.02% to about 1% (w/w) in the organic phase.

B. Porous Polymeric Substrates

The porous polymeric substrate may be prepared from any suitable polymer. Preferably the porous polymeric substrate is formed from a material that is not spontaneously wetted by water, and is compatible with the organic phase used to form the liquid membrane. The polymer may be a homopolymer or copolymer, where the copolymer includes terpolymers or more complex polymers, and can be a single polymer or a combination of two or more polymers. The polymer may be subjected to a pretreatment, for example, sulfonation or grafting prior to forming the porous polymeric substrate, or may be subjected to a post-treatment, for example grafting or crosslinking, after the porous polymeric substrate is formed. There is no particular molecular weight range limitation for useful polymers.

Examples of materials suitable for such supports include polyolefins, sulfone polymers such as polysulfone, polyethersulfone, or polyarylsulfone, fluorinated polymers such as polyvinylidene fluoride (PVDF), acrylic copolymers, polyamides or nylons, polyesters, polyurethanes, polycarbonates, polystyrenes, polyvinyl chlorides, polyacrylonitriles, or copolymers thereof or mixtures thereof. In a particularly preferred embodiment, the polymer is a polyolefin such as polyethylene, polypropylene, polytetrafluoroethylene (PTFE), poly(tetrafluoroethylene-co-ethylene) (ECTFE), or polyethylene-polyvinyl chloride copolymer. Additional examples for polyolefins include polymers of monoolefins and diolefins, for example polyisobutylene, polybut-1-ene, poly-4-methylpent-1-ene, polyisoprene or polybutadiene, as well as polymers of cycloolefins, for instance of cyclopentene or norbornene, as well as copolymers of monoolefins and diolefins, with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/ acrylic acid copolymers and their salts (ionomers), as well as terpolymers of ethylene with propylene and a diene such as hexadiene, dicyclopentadiene or ethylidene-norbornene; and mixtures of such copolymers with one another and with polymers mentioned above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides. Mixtures of polymers, for example, mixtures of polypropylene with polyisobutylene, polypropylene with polyethylene (for example PP/HDPE, PP/LDPE) and mixtures of different types of polyethylene (for example LDPE/HDPE) can also be used. The polymeric substrates may be treated to alter their surface properties. For example, polyethylene films may be treated with chromic acid to render the films less hydrophobic.

In addition, the porous polymeric substrates can be covalently modified or combined in proportions to incorporate selectivity features which would permit the isolation of a single analyte from a complex mixture or a group of analytes from other groups or exclude unwanted materials from human fluids or synthetic reaction mixtures. Thus, substrates made from different polymeric materials (such as polypropylene, polysulfone, polycarbonate or polyether sulfone, etc.) can be utilized to harness selectivity arising from interactions of analytes with the polymer. Alternatively, the polymeric substrates can be coated with different membrane forming liquids to utilize membrane-based selectivity for optimization of enrichment and selective extraction. The chemistry of the acceptor solutions (strong or weak acids or bases, for example) as well as the pH of the acceptor solutions can be varied along with variation of the polymer chemistry, to achieve the desired separation. Furthermore, the pore size of the fibers can also be varied to effect selective diffusion across the polymeric substrate and liquid membrane.

The porous polymeric substrate is an open-celled, interconnected structure providing an open network that supports the liquid membrane. The pores of suitable microporous materials are in the range of about 0.01 to about 500 microns, or more typically up to about 10 microns in effective diameter. In many instances, the polymeric substrates are commercially available, although they can be synthesized by polymerization methods known in the art. A specific pore size is not necessarily important in a given application. Pore sizes of 0.2 µm are generally satisfactory in the systems tested here.

Porosity is defined as the fractional volume of the membrane that is open rather than substrate material. Typical commercial hollow fibers have a porosity of about 30 to 80%. A commercially-available Celgard® (Celanese Separations Products, Charlotte, N.C.) polypropylene membrane, for example, has a porosity between 40 and 50%. Larger pore sizes and greater porosity result in maximal permeability to analytes, but mechanical stability may be decreased. A porosity of about 70% is generally satisfactory.

Typically, the thickness of the polymeric substrate ranges from between 10 and 300 microns, although thicker supports can be used for certain applications. The mechanical strength can be compromised if the wall thickness is too low. For polypropylene, a thickness of 200 microns appears to be optimal for balancing mechanical strength with extraction time, since the rate of extraction will be reduced if the thickness is increased too much because of the long diffusion distance from the sample solution to the acceptor solution.

The porous polymeric substrates can be in any suitable shape or form. Suitable forms include, but are not limited to, substantially planar forms such as sheets, disks, or cones, tubular shapes such as hollow fibers, which can be open at both ends or closed at one end, helical or spirally wound, or spherical shapes. An exemplary form is a hollow fiber cast polymer membrane. The hollow fiber form of the polymeric substrates (in comparison with a flat sheet), especially in helical or spirally wound formats, provides a high ratio of support surface area to volume of the sample solution and acceptor solution and facilitates analyte extraction. Such hollow fibers can be conveniently inserted into sample containers such as sample vials, one embodiment of which is shown in FIG. 1, or microtiter plates, two embodiments of which are shown in FIG. 2. Use of hollow fibers also allows for convenient introduction and removal of acceptor solutions and/or sample solutions. Planar structures such as disks or sheets can also be used, and can be flat or curved, as shown, for example, in FIGS. 4A and B, respectively.

C. Acceptor Solutions

Acceptor solutions to be used in LPME include aqueous solutions that can optionally comprise salts, buffers, acids, bases, conditioning agents, preservatives, and the like. The composition of the acceptor solution is chosen so that the acceptor solution is capable of accepting at least one analyte of interest from the sample. Preferably, the acceptor solution provides a means for trapping analytes in the acceptor phase after partitioning of the analyte into the organic phase forming the liquid membrane, and solvation of the analyte in the acceptor solution. The acceptor solution generally comprises an aqueous solution, having a pH above or below the pKa of titratable groups on the analytes of interest in the samples to be extracted using LPME, but other methods of trapping analytes can be provided in the acceptor solution.

In one embodiment, the analyte is trapped in a less permeable charged form in the acceptor solution after first partitioning into the organic phase and traversing the organic phase to equilibrate in the acceptor phase. For example, enrichment of a carboxylic acid analyte is effected from a sample by adjusting the pH of the sample solution below the pKa of the acid so that the carboxylic acid is neutralized and partitions into the liquid membrane, while the pH of the acceptor aqueous solution is above the pKa of the acid, causing the analyte diffusing into the acceptor solution to be trapped in its ionized form. Similarly, extraction of a basic analyte is effected using a basified sample solution and an acidified acceptor solution.

However, any modification of the analyte in the acceptor phase resulting in decreased partitioning and permeability in the organic phase can be used to trap and enrich analytes in the acceptor phase. Therefore, additional trapping means are possible. For example, alternative trapping means include: the presence of metals ions that could promote formation of an analyte-metal chelate; aqueous conditions such as high ammonium sulfate concentrations promoting precipitation or the formation of an analyte complex of higher molecular weight; covalent modifiers effecting covalent modification of the analytes; ligands that bind the analytes with high affinity, etc.

D. Single or Multiple Use Applications

The devices for performing liquid phase microextraction can be designed for single use or high throughput applications. High-throughput screening involves the automated analysis of large numbers of samples within short time frames. Samples are generally purified and extracted directly using the autosampler systems of analytical instruments, and aliquots from the purified and extracted sample solutions can be injected directly into the analytical instrument. The devices can be used in the liquid phase microextraction of analytes from a sample solution contained in any sample container, whether made of a polymer, glass, metal, or the like, without limitation.

In one embodiment, the porous polymeric substrate is in the form of a hollow fiber and can be used to extract analytes from a single sample solution, such as contained in a sample vial, by a human operator or autosampler. Alternatively, an assembly of hollow fibers can be used to extract analytes from many sample solutions in parallel. For example, hollow fibers can be designed to conveniently fit into 48, 96, 384, 1536 (or greater) well microtiter plates. An illustration of an assembly of hollow fiber extraction membranes is shown in FIG. 2A. In one embodiment, a cover plate of a 96 well microtiter plate, carrying polypropylene fibers of 0.5 cm to 8 cm in length, 600 µm inner diameter and 0.2 µm pore size, can be prepared by dipping the fibers into the liquid membrane organic phase contained in the wells of a 96 well plate for about 5 seconds. The fibers in the cover plate can then optionally be rinsed or sonicated in water for 15 seconds to remove excess material sticking to the fibers, and stored in an empty 96 well plate until use. As shown in FIG. 2B, the acceptor solution can be conveniently sampled from the lumen of the hollow fiber through the opening in the top plate leading to the lumen. In FIG. 2C, a top plate design is shown where the sample solution can be easily added or removed through an opening in the top plate, while the access to the acceptor solution is not depicted in this view. In alternative embodiments, the wells can contain the acceptor solution and the hollow fibers can contain the sample solution to be analyzed.

FIG. 3 illustrates three additional embodiments of hollow fiber and sample container geometries. For example, FIG. 3A and FIG. 3C depict two different hollow fiber geometries that facilitate filling the hollow fiber without the introduction of bubbles. The device shown in FIG. 3C is also readily adapted to a flow through system where one access port can be used to introduce additional acceptor solution, for example, and the other access port can be used to remove acceptor solution enriched in analytes. This arrangement is convenient for analyzing changes in analyte concentration or composition as a function of time, for example, for observing the course of a synthetic reaction, metabolic decomposition of a drug, or in situ production of chemical or biological agent by a cell or tissue culture. FIG. 3B illustrates yet another embodiment of a hollow fiber geometry providing two inlet ports, allowing the two different lumen portions of the hollow fiber to be sampled separately, depending on the amount of acceptor solution added. Although depicted as constructed in one piece, the polymeric substrate forming the hollow fiber can be formed in separate pieces and joined together or joined with the material forming the top plate. Additional embodiments shown in WO 02/088672 can also be adapted using the liquid membranes and methods of preparation disclosed herein.

Extraction and purification can be carried out by automatic or manual delivery of sample solutions into the wells using fibers containing the acceptor solution, which can be manually or automatically delivered into the lumen of the fibers. The autosampler injector needle of the chromatographic instrument, for example, can pick up the enriched and extracted sample directly from the hollow fiber and deliver it to the instrument for analysis. The well plate assembly can be mounted directly onto the analytical instrument if desired. Alternatively, the sample enrichment process can be carried out in autosampler vials, as shown schematically in FIG. 1, which are commonly used in liquid chromatographic instruments. A miniature device can incorporate hollow fibers into each of the vials individually. The ends of these fibers can be connected to appropriate inlet/outlet ports located in the cap portion of the vials for automated delivery and withdrawal of acceptor solution before and after enrichment, respectively. Thus, the devices provide for enriching and analyzing multiple samples at a time through an automated sampling system.

Planar structures such as disks or sheets can also be used. As shown in FIGS. 4A and B, a disk or cone-shaped polymer substrate having a liquid membrane supported thereon can be used as the bottom of an acceptor well or in an assembly of such wells, such as a 96 well plate, and inserted into sample solutions for performing extraction. Acceptor solutions can be conveniently added to the open top of the acceptor wells, or the wells can be closed except for an access orifice into which the acceptor solution can be injected and from which it can be removed for assay.

One skilled in the art will readily envision additional embodiments involving flow through sample and/or acceptor solution directly to analytical instrumentation or sample collectors. In addition, the supported liquid membranes can in principle be incorporated into microfluidics devices and used in microfluidics applications.

III. Methods for Preparing Liquid Membranes for LPME

Methods are also provided for preparing a liquid membrane on a porous polymeric substrate for performing liquid phase microextraction. The methods generally comprise the step of applying an organic phase comprising a fatty acid ester, a vegetable oil, a silicone oil, a nitroarylalkylether, or mixtures thereof to a porous polymeric substrate to form a liquid membrane on the porous polymeric substrate. In certain embodiments, the porous polymeric substrate is in the form of a hollow fiber. In other embodiments, the porous polymeric substrate is in a substantially planar form, such as a sheet or disk. The methods can further comprise removing excess organic phase, such as by sonicating or rinsing the porous polymeric substrate, or withdrawing excess organic phase using a syringe. Once formed, the devices for performing LPME can be stored, preferably in a covered contained in air until use. Storage under other atmospheric conditions, such as in an argon or nitrogen atmosphere, or in the absence of water, can also prove advantageous.

The organic phase can be applied to the porous polymeric substrate using any method. For example, the organic phase can be painted, dripped, sprayed, onto the porous polymer, or the porous polymer can be inserted, soaked, dipped, etc. into the organic phase, without limitation. In one embodiment, supported liquid membranes are formed on porous hollow fibers by dipping the hollow fiber into the organic phase for a brief period of time (e.g., 5 to 30 seconds) to allow the solvent to penetrate into the pores of the fiber. Excess organic phase can optionally be removed by allowing the excess to drip off the fibers, or can be removed by brief rinsing or sonication in water or other aqueous solution. Acceptor solution can be introduced into the lumen of the fiber using a syringe. In this manner, coated fibers can be easily prepared and stored.

In another embodiment, supported liquid membranes are formed on porous hollow fibers by introducing the organic phase into the lumen of the fiber for a brief period of time (e.g., 5 to 30 seconds). Excess organic phase can be removed, e.g., using a micro syringe or a pipette. Acceptor solution can then be introduced into the lumen of the fiber using a syringe when ready for use.

In yet another embodiment, a substantially planar supported liquid membrane can be formed by any method for placing the organic phase on the surface of the planar porous membrane. For example, the organic phase can be painted, dripped, sprayed, onto the porous membrane, without limitation. The porous membrane can also be immersed into the organic phase. The excess organic phase is allowed to drain away or can be removed, e.g. by use of a syringe or pipette, or by brief rinsing or sonication in aqueous solution. A planar supported liquid membrane can be formed on the membrane prior to assembly in an extraction apparatus, or can be formed on a prefabricated porous membrane extraction device.

LPME can also be performed using a microtiter plate or well format device. Briefly, a cover plate of a 96 well block, carrying polypropylene fibers of 0.5 cm to 8 cm in length, 600 µm inner diameter and 0.2 µm pore size, can be dipped into the liquid membrane organic phase contained in the wells of a 96 well plate for about 5 seconds. The fibers in the cover plate can then optionally be rinsed or sonicated in water for 15 seconds to remove excess material sticking to the fibers, and stored in an empty 96 well plate prior to use.

IV. Methods for Performing LPME

A method for performing liquid phase microextraction of at least one analyte from a sample solution is provided, comprising contacting the sample solution containing the at least one analyte with one side of a liquid membrane having two sides formed on a porous polymeric substrate, and contacting an acceptor solution with a second side of the liquid membrane. The extraction can be continued for a time sufficient to allow transfer of the analyte to the acceptor solution, generally 15-60 minutes. However, the time for performing the extraction can be increased or decreased depending on the concentration of the analyte in the sample solution, the detection limits of the assay procedure used to detect the analyte in the acceptor solution, the liquid membrane composition, the partition coefficient of the analyte into the liquid membrane, and the composition of the sample and acceptor solutions. The sample solution, the acceptor solution, or both solutions can be agitated, such as by stirring by magnetic or mechanical means.

In another preferred embodiment, the porous polymer substrate is a hollow fiber, and the acceptor solution is contained within the hollow fiber. In this embodiment, the method of performing LPME is generally a simple step of introducing the LPME device into the sample solution. For example the hollow fiber having a supported liquid membrane can be introduced into the sample solution, directly in the sample vial, test tube or well plate, for example. The lumen of the fiber can be filled with acceptor solution before the hollow fiber is introduced to the sample or after. The extraction is performed by allowing analytes to concentrate in the acceptor solution, and can be continued until the analytes reach equilibrium between the sample solution and the acceptor solution or can be terminated at any point simply by removing the hollow fiber or by withdrawing the acceptor solution from the hollow fiber. Equilibrium is usually reached in LPME procedures in 15 to 60 minutes. It is not necessary that a true equilibrium be reached between the sample and acceptor solutions, and the equilibration time can be as little time as is required to result in enrichment of the analyte in the acceptor solution. In some instances, equilibration can be hastened by agitating the sample solution, such as by stirring or vibration, or by increasing the temperature at which the extraction is performed. The acceptor solution can then be withdrawn from the lumen of the hollow fiber using a syringe, and concentrated further, diluted with additional acceptor solution, or used directly for injection into an analytical instrument.

The extraction can be performed in a static mode or an active mode. By "static" is meant that the sample solution and the acceptor solution remain in contact with the liquid membrane during the extraction and no additional sample or acceptor solution is introduced while the extraction is being performed. Extractions can be completed in about 15 minutes and sample enrichments ranging from 30 to 200 fold can be achieved. Such high levels of sample enrichment are not commonly achievable with presently-available standard sample preparation techniques. "Active" extraction indicates that additional sample or acceptor solution is introduced while the extraction is being performed. Active extraction can include flow-through embodiments, where additional sample solution, acceptor solution or both are pumped through the extraction system, for example, in a continuous feed manner.

Figure 5:
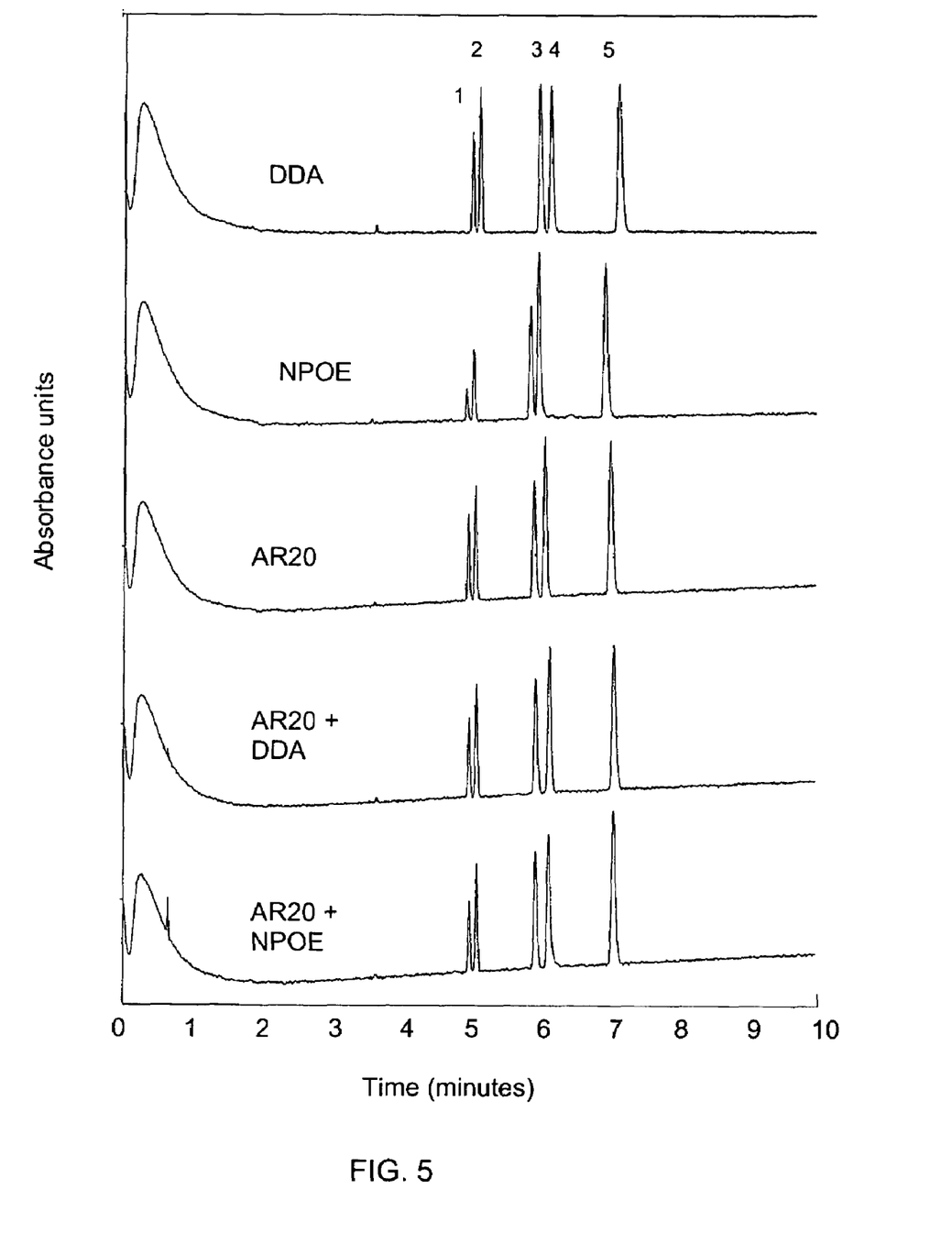
FIG. 5 shows capillary electrophoregrams of analytes extracted from identical samples by supported liquid membranes of different organic phases formed on porous hollow fibers that had been stored for 30 days.

Sample solution to acceptor liquid ratios ranging from about 5:1 to 200:1 can be employed. Thus, one has the choice of using sample solution volumes from about 10 µL to about 10 L, more conveniently from about 100 µL to about 10 mL, although the method is not limited to any particular volume of sample solution, and these volumes can vary according to the analyte concentration, volume needed for analysis, sensitivity of the analytical instrumentation, and the needs of the practitioner. In embodiments illustrated in the Examples below, a sample volume of 4 mL and an acceptor solution of 25 µL was utilized, although one will readily envision additional sample and acceptor volumes that can be conveniently used. For hollow fiber extraction devices, the acceptor volume desired can be controlled by fiber inner and outer diameter and fiber length. If it is desired to concentrate the analyte into a very small volume, a fiber having a small inner and outer diameter is chosen In exemplary embodiments described in Examples 3 and 4, extraction ability was tested by immersing the hollow fibers with their supported liquid membranes into sample vials containing 4 mL of a solution containing 5 different drugs: amphetamine, methamphetamine, pethidine, chlorcyclizine and haloperidol at a concentration of 100 ng/ml and a pH of 12. Extraction was performed with stirring, and the analytes were allowed to equilibrate across the liquid membrane to the acceptor solution of 25 µl 10 mM HCl. After allowing the sample analytes sufficient time to reach equilibration with the acceptor solution, about 15 to 60 minutes, the acceptor solution was withdrawn from the hollow fibers, and the concentration of analytes was determined using capillary electrophoresis. The results shown in FIG. 5 demonstrate the stability of the liquid membranes after storage for 30 days.

The analyte that can be extracted can comprise virtually any species which is soluble in both the sample and acceptor solutions. Both organic and inorganic species can be enriched and purified by means of the present invention. Further, polymeric species, such as peptides or peptidomimetic compounds, can in principle be enriched into the acceptor solution. Still further, multiple solute species can be separated by the present invention. Preferred solutes comprise biological compounds, such as, but not limited to, drugs, diagnostic agents, natural products, compounds produced by genetically engineered organisms, enzymes and enzyme cofactors, vitamins, and hormones. Still further, the present methods can be used to extract other inorganic and organic species, including pesticides, pollutants (e.g., PCBs, trichloroethylene, and benzene), organic compounds and halogenated organic compounds, synthetic compounds (including compounds from combinatorial libraries), fuels, petrochemicals, salts, metal ions, including metal complexes and organic metallic compounds, and mixtures thereof.

Generally, the sample solution is a biological sample or an environmental sample. Alternatively, the sample can be prepared from a dispersion of any solid matter in aqueous solution, including soil, food, plant matter, animal tissues, fungal or bacterial matter, waste materials, or aqueous samples of dissolved airborne compounds. The biological sample can be, for example, urine, plasma, blood, lymph, cerebrospinal fluid, tears, sweat, gastrointestinal fluids, mucous secretions (e.g., saliva, vaginal secretions, etc.), or cell culture fluid. The environmental sample can be, for example, condensed water (i.e., water obtained from a surface such as a building, machine, or other solid object, or recovered from a sample on heating, combustion or reaction), surface water, ground water (including subsurface water or aquifer water), rain water, river water (including streams of all sizes), sea water, lake water, effluent water (from a sewer, manufacturing facility, runoff water, etc.), influent water, or drinking water.

In exemplary embodiments, LPME can be used to extract drugs for analysis from a biological sample containing drugs, including neutral, acidic or basic drugs, or mixtures thereof. The sample solution containing drugs, for example, can be diluted with water so that the concentration of the drugs is in the range of 0.01 to 5 µg/mL and the pH is adjusted with sodium hydroxide, hydrochloric acid, or an appropriate buffer to the desired pH, and used for extraction. The final concentration of drugs in the sample solution can be adjusted to any desired range. Preferably the drugs are acidic or basic and can be enriched in the acceptor solution by adjusting the pH of the acceptor solution so that the analyte is trapped in an ionized or less permeable form in the acceptor solution. In one embodiment, the drug is a basic drug, and the acceptor solution is acidic, such as by adjusting the acceptor solution by adding 0.1 M hydrochloric acid.

Examples of drugs that can be extracted using LPME include, without limitation, analgesics such as ibuprofen, ketoprofen, paracetamol, acetylsalicylic acid, acetaminophen; COX-2 inhibitors such as nimesulide, meloxicam, naproxen, propyphenazone, metamizole; antacids such as hydrotalcite, magaldrate, calcium carbonate;

antiasthmatics/bronchospasmolytics such as salbutamol, tulobuterol, terbutaline, cromoglicic acid, ketotifen, theophylline; antibiotics such as quinolones, tetracyclines, cephalosporins, penicillins, macrolides, sulphonamides; psychopharmaceuticals including sedatives such as benzodiazepines (e.g., diazepam), haloperidol, carbamazepine and antidepressants such as amitriptyline, citalopram and sertraline; antirheumatics such as phenylbutazone, indomethacin, diclofenac, piroxicam; antidiabetics such as metformin, glibenclamide, acarbose, glipizide, glisoxepide; antiallergics/antihistamines such as astemizole, terfenadine, loratadine, clemastine, bamipine, cetirizine and chlorcyclizine; antihypotensives such as etilefrine, norfenefrine, dihyroergotamine mesilate; antitussives such as codeine, dextromethorphan, clobutinol, dropropizine and noscapine; antihypertensives such as beta blockers (e.g., propranolol, atenolol, metoprolol, prazosin), calcium channel blockers (e.g., nifedipine, nitrendipine, diltiazem, verapamil, felodipine, nimodipine) and sympatholytics, such as reserpine; laxatives such as sodium picosulphate, lactulose, lactitol; mucolytics/expectorants such as ambroxol, bromhexine, guaifenesin, acetylcysteine, carbocisteine; histamine $H_2$ blockers such as ranitidine, famotidine, pirenzepine; local anesthetics such as benzocaine, lidocaine, procaine; opiates such as methadone, buprenorphine, pethidine and tramadol; antiemetics/prokinetics such as metoclopramide, domperidone, meclozine, dimenhydrinate; lipid-lowering agents such as fenofibrate, bezafibrate, pravastatin, fluvastatin; agents effective for migraine, such as caffeine, dihydroergotamine, ergotamine, sumatriptan, pizotifen; symnpathomimetics such as pseudoephedrine, pholedrine; stimulants such as amphetamine and methamphetamine. One skilled in the art will appreciate that there are numerous other examples of drug species that can be extracted using the methods disclosed herein.

After the extraction is completed, the acceptor solution, now enriched in analytes, can be analyzed using any analytical device suitable for the particular analyte, such as high performance liquid chromatography (HPLC), capillary electrophoresis, capillary electrochromatography, gas chromatography, mass spectrometry, and so forth. For example, the analytes can be characterized by HPLC using an Omnisphere C18 column and a mobile phase of acetonitrile/pH 7.0 dipotassium hydrogen phosphate, or a gradient of 5% acetonitrile to 40% to elute the strongly retained components in a reasonable time frame. Using this approach, over 100 to 200 fold enrichments of the basic drugs quinidine and doxepin have been demonstrated.

LPME can also be performed using a well format device. Briefly, a cover plate of a 96 well block, carrying polypropylene fibers of 0.5 cm to 8 cm in length, 600 µm inner diameter and 0.2 µm pore size, can be dipped into the liquid membrane organic phase contained in the wells of a 96 well plate for about 5 seconds. The fibers in the cover plate can then optionally be rinsed or sonicated in water for 15 seconds to remove excess material sticking to the fibers, and stored in an empty 96 well plate prior to use.

It will be clear to one skilled in the art that the above embodiments may be altered in many ways without departing from the scope of the invention. Although 96 well block formats are described, many other multi-well formats can be applied for the same LPME purpose, such as 48, 24, 384 or 1536 well formats, etc. Single or multiple hollow fibers can be connected to each of the wells or vial caps.

It is understood that any recited steps need not be performed in the exact order listed in a given claim. Accordingly, the scope of the invention should be determined by the following claims and their legal equivalents. It is to be understood that while the invention has been described in conjunction with the preferred specific embodiments thereof, that the description above as well as the examples that follow are intended to illustrate and not limit the scope of the invention.

The practice of the present invention will employ, unless otherwise indicated, conventional techniques of organic chemistry, polymer chemistry, biochemistry and the like, which are within the skill of the art. Other aspects, advantages and modifications within the scope of the invention will be apparent to those skilled in the art to which the invention pertains. Such techniques are explained fully in the literature.

In the following examples, efforts have been made to ensure accuracy with respect to numbers used (e.g., amounts, temperature, etc.) but some experimental error and deviation should be accounted for. Unless indicated otherwise, temperature is in degrees ° C. and pressure is at or near atmospheric. All solvents were purchased as HPLC grade. Unless otherwise indicated, the reagents used were obtained from the following sources: Sigma (St. Louis, Mo., USA). Hollow polypropylene fibers having pores of 0.2 µm were purchased from Membrana (Wuppertal, Germany). The hollow fibers possessed an inner diameter of 600 µm, the wall thickness was 200 µm, and the length was 5.5 cm. For some experiments, hollow fibers of polysulfone were used.

| Abbreviations: | |
|---|---|
| dodecyl acetate | DDA |
| nitropheyloctyl ether | NPOE |
| silicone oil AR 20 | AR 20 |
| amphetamine | A |
| methamphetamine | M |
| pethidine | P |
| chlorcyclizine | C |
| haloperidol | H |
| trioctylphosphine oxide | TOPO |

EXAMPLE 1

Stability of Liquid Membranes Immobilized on Hollow Fibers

Initial experiments were performed using n-octanol or dihexyl ether as the organic solvent immobilized in the pores of hollow fibers constructed from polypropylene. These solvents were selected based on their low polarity, hydrophobic capillary attraction forces to the pores of the hollow fibers, low volatility, intermediate solubility for analytes, and low viscosity resulting in acceptable analyte permeability. Liquid membranes comprising n-octanol or dihexyl ether were prepared using the following procedure:

The liquid membrane was formed by dipping the hollow fiber into the organic solvent for 5 to 30 sec to allow the solvent to penetrate into the pores of the fiber. Then acceptor solution was introduced into the lumen of the fiber using a syringe. The acceptor solution was 10 mM HCl, having a pH of 2. Extraction ability was tested by immersing the hollow fibers with their supported liquid membranes into a sample vial containing 4 mL of a solution containing 5 basic drugs, at a pH of 12, with stirring, and allowing the analytes to equilibrate across the liquid membranes to the acceptor solution within (25 µl 10 mM HCl). After allowing the sample analytes sufficient time to reach equilibrium with the acceptor solution, about 15 to 60 minutes, the acceptor solution was withdrawn from the hollow fibers, and the concentration of analytes was determined using capillary electrophoresis.

When supported liquid membranes were used immediately after being prepared, good extraction results were observed. However, when the supported membranes were stored for a few days, the fibers failed to extract analytes due to disruption of the liquid membrane. The weights of the hollow fibers were determined immediately after preparation and then after storage, but were found to be unchanged, indicating that the solvent had not evaporated. It was concluded that both solvents swelled into the polypropylene supports resulting in disruption of the liquid membrane. It was concluded that new solvents were needed that would be stable over long periods of time in order to develop a pre-coated product with acceptable stability.

EXAMPLE 2

Stability of Fatty Oil Liquid Membranes Immobilized on Hollow Fibers

Experiments were performed using polypropylene and polysulfone hollow fibers, testing the effectiveness and stability of liquid membranes comprising fatty oils in the extraction of analytes from samples after storage of the fibers for 30 days prior to use. Supported liquid membranes were established on the hollow fibers using the procedures described in Example 1 above, but substituting the following oils for the organic solvents tested in Example 1: tributyrin, soya oil, or olive oil. When fibers were to be stored, they were stored at room temperature attached to syringe needles mounted in a screw cap and placed in 4 mL vials. The fibers were therefore mechanically protected, but air was able to penetrate into the system through the needles and the system was not completely closed. The fibers were stored for 30 days in this manner, and tested as described above.

The supported liquid membranes of tributyrin formed on polypropylene fibers extracted analytes after 30 days of storage. Liquid membranes formed from olive oil and soya oil also resulted in acceptable performance after 30 days of storage, and in some instances the solutions became cloudy.

Most of the liquid membranes formed on polysulfone fibers stored for 30 days were not usable for liquid phase microextraction due to leaks, and it was observed that the mechanical stability of the polysulfone material was compromised.

EXAMPLE 3

Stability of Liquid Membranes Immobilized on Hollow Fibers

A new study was initiated to prepare and test liquid membranes formed on porous hollow fibers of polypropylene from additional solvent candidates that were ideally chemical substances of high inertness or alternatively a mixture of components with high chemical stability. Liquid membranes composed of dodecyl acetate (DDA), nitropheyloctyl ether (NPOE), and silicone oil AR 20 (AR 20) were tested both alone and in combination. The fibers were stored under the same conditions as described in Example 2. Extraction of 5 different drugs was performed as described in Example 1 using the fibers that had been stored for 30 days. With DDA and NPOE, some of the sample solutions became unclear during the extraction, which indicated that the organic phase was partially removed from the fiber to the sample solution. However, with AR 20, this problem was not observed. The recovery of the 5 different drugs was measured for each of the experimental systems described above, and the results are presented in Table 1 below and in FIG. 5. The 5 different drugs extracted were amphetamine (A), methamphetamine (M), pethidine (P), chlorcyclizine (C) and haloperidol (H) at 100 ng/mL and pH 12. The experimental results obtainable from fibers which had not been stored were not determined for comparison in this experiment, but the recovery values were high and indicated that no significant loss of performance occurred during the 30 days of storage.

TABLE 1

Recovery of five different drugs using liquid membranes formed from different organic phases

| organic phase | Recovery (%) | | | | |
|---|---|---|---|---|---|
| | A | M | P | C | H |
| DDA | 63 | 87 | 101 | 85 | 89 |
| NPOE | 20 | 52 | 99 | 99 | 105 |
| AR 20 | 54 | 79 | 92 | 84 | 87 |
| DDA + AR 20 (1:1) | 54 | 83 | 97 | 89 | 96 |
| NPOE + AR 20 (1:1) | 53 | 86 | 109 | 90 | 111 |

EXAMPLE 4

Stability of Liquid Membranes Immobilized on Hollow Fibers Over a 90 Day Period

A comprehensive stability study was performed over a 90 day period of time, using liquid membranes formed on porous polypropylene hollow fibers as described in Example 1, using the organic phases shown in Table 2. The ability of the fibers to extract drugs from samples was determined as described in Example 3, after 0, 60 and 90 days of storage. The fibers were stored as described in Example 1, protected from mechanical stress by storage in vials, but in contact with the air. The organic phases tested were as follows: silicon oil AR 20 (AR 20), nitrophenyloctyl ether (NPOE), dodecyl acetate (DDA), soya oil, tea tree oil, peppermint oil, AR 20+tea tree oil (1:1) and AR 20+5% trioctylphosphine oxide (TOPO). Liquid membranes formed from tea tree oil and peppermint oil alone failed to extract the drugs. These two phases when used alone either evaporated or were absorbed into the polypropylene, and failed to extract the drugs. The remaining organic phases exhibited acceptable performance, as summarized in Table 2.

TABLE 2

Recovery of five different drugs using liquid membranes formed from different organic phases

| organic phase | Recovery (%) | | | | |
|---|---|---|---|---|---|
| | A | M | P | C | H |
| AR 20 day 0 | 46 | 73 | 81 | 74 | 78 |
| AR 20 day 60 | 51 | 79 | 85 | 75 | 75 |
| AR 20 day 90 | 57 | 89 | 105 | 96 | 98 |
| NPOE day 0 | 24 | 62 | 107 | 106 | 110 |
| NPOE day 60 | 21 | 52 | 94 | 105 | 102 |
| NPOE day 90 | 23 | 55 | 90 | 100 | 101 |
| DDA day 0 | 57 | 94 | 104 | 77 | 85 |
| DDA day 60 | 58 | 90 | 101 | 88 | 93 |
| DDA day 90 | 65 | 103 | 100 | 98 | 108 |
| Soya oil day 0 | — | — | — | — | — |
| Soya oil day 60 | 14 | 34 | 59 | 99 | 81 |
| Soya oil day 90 | 13 | 31 | 49 | 79 | 69 |
| AR20 + tea tree oil day 0 | — | — | — | — | — |
| AR20 + tea tree oil day 60 | 18 | 40 | 59 | 78 | 60 |
| AR20 + tea tree oil day 90 | 17 | 35 | 56 | 87 | 51 |
| AR20 + TOPO day 0 | — | — | — | — | — |
| AR20 + TOPO day 60 | 44 | 82 | 109 | 117 | 108 |
| AR20 + TOPO day 90 | 40 | 74 | 92 | 102 | 92 |

As seen from the data presented in Table 2, all of the organic phases extracted the drugs with almost the same efficiency after 0, 60 and 90 days of storage. Minor differences were observed in percent recovery as a function of storage time, but the differences were within the experimental error of the assay. The liquid membranes formed from AR 20 alone or in combination with TOPO, and from the fatty acid ester DDA, appeared to provide the greatest recovery of the drugs from the sample solutions.

These results demonstrate that organic phases such as DDA, NPOE, AR 20, tributyrin can be prepared as liquid membranes on polypropylene hollow fibers and stored for at least 90 days at room temperature without disruption of the liquid membranes. These results demonstrate an advance in the art over previous work which demonstrated that the liquid membranes were not stable for more than a few days, and therefore should be prepared fresh before each use.

EXAMPLE 5

Weights of Fatty Acid Ester Liquid Membranes Stored under Different Conditions Experiments were conducted to evaluate fatty acid esters as organic phases for liquid phase microextraction. Liquid membranes were formed on porous polypropylene hollow fibers prepared as described in Example 1 using DDA as the organic phase. The fibers were stored either in the open air (5 samples) or in a closed container (10 samples). The fibers were weighed on day 0, days 2, 3, 5 and 10. The results are shown in Table 3 below.

TABLE 3

Weights of fibers prepared with liquid membranes of DDA as a function of time and stored under different conditions

| Storing condition | Weight (mg) | | | | |
|---|---|---|---|---|---|
| | Day 0 | Day 2 | Day 3 | Day 5 | Day 10 |
| Closed container | 42.40 | | 42.14 | | 42.12 |
| Open to the air | 45.94 | 43.92 | | 41.70 | |

The results presented in Table 3 demonstrate that liquid membranes formed from DDA stored open to the air exhibited weight loss, consistent with evaporation of a small amount of the DDA from the fiber. However, the weight loss was prevented when the fibers were stored in a closed container Based on these results, an additional experiment was performed to determine the stability of liquid membranes formed using myristoyl acetate (MA) instead of DDA. Myristic acid is a 14 carbon chain, and is two carbons longer than lauric acid (the 12 carbon chain of DDA). Myristic acid therefore has a higher boiling point, and is less volatile than DDA and would be expected to exhibit less evaporation. The results for the experiments performed using myristoyl acetate are shown in Table 4 below.

TABLE 4

Weights of fibers prepared with liquid membranes of MA as a function of time and stored under different conditions

| Storing condition | Weight (mg) | |
|---|---|---|
| | Day 0 | Day 4 |
| Closed container | 38.76 | 38.72 |
| Open to the air | 41.36 | 40.90 |

The results presented in Table 4 demonstrate that less evaporation of MA occurred when the fibers were stored in closed containers, although the evaporation was reduced relative to that observed for DDA liquid membranes. However, it was concluded that the best performance of the liquid membranes hollow fibers would be obtained by storing the fibers in closed containers prior to use.

What is claimed is:

1. A device for performing liquid phase microextraction of at least one analyte from an aqueous sample comprising a liquid membrane supported on a porous polymeric substrate, wherein said liquid membrane has one side that can be placed in fluid communication with the aqueous sample containing the at least one analyte and a second side that can be placed in fluid communication with an acceptor solution, and wherein said liquid membrane comprises a fatty acid ester, wherein said fatty acid ester comprises an acyl chain comprising from 12 to 30 carbon atoms.

2. The device of claim 1, wherein said porous polymeric substrate is a hollow fiber.

3. The device of claim 1, wherein said fatty acid ester comprises an ester portion comprising from 1 to 12 carbon atoms.

4. The device of claim 1, wherein said liquid membrane further comprises a vegetable oil.

5. The device of claim 1, wherein the liquid membrane further comprises a carrier.

6. The device of claim 5, wherein the carrier is an organic ion, an ionophore or a pore forming agent.

7. The device of claim 6, wherein the carrier is an organic ion.

8. The device of claim 7, wherein the organic ion is trioctyiphosphine oxide (TOPO), diethyihexyl phosphoric acid, triethylhexyl phosphoric acid, dodecylbenzene sulphonic acid, aliquat 336 (trioctylmethylammonium chloride), amberlite LA, tri-n-octyl amine, tetraphenylphosphonium, tetraphenylarsonium, trinitrophenol, or tetraphenylboron.

9. The device of claim 1, wherein said polymeric substrate comprises a polyolefin, acrylic copolymer, polyamide, polyester, polyurethane, polycarbonate, polystyrene, fluorinated polymer, polyvinyl chloride, polyacrylonitrile, copolymers thereof, or mixtures thereof.

10. The device of claim 9, wherein the polymeric substrate comprises a polyolefin.

11. The device of claim 10, wherein the polyolefin is polyethylene, polypropylene, polytetrafluoroethylene, poly(tetrafluoroethylene-co-ethyl-ene), or polyethylene-polyvinyl chloride copolymer, copolymers thereof, or mixtures thereof.

12. The device of claim 1, wherein said liquid membrane is stable for at least 30 days, 60 days or 90 days.

13. The device of claim 2, wherein said hollow fiber is able to extract at least one analyte after being stored for at least 30 days, 60 days or 90 days.

14. The device of claim 1, wherein in operation, the acceptor solution is placed inside the hollow fiber and the hollow fiber is placed in the sample solution.

15. The device of claim 1, wherein the acceptor solution can be sampled by an autosampler.

16. A device for carrying out liquid phase microextraction of at least one analyte from an aqueous sample, said device comprising a hollow fiber comprised of a porous polymeric substrate and a liquid membrane supported thereon, wherein said liquid membrane comprises a fatty acid ester, wherein said fatty acid ester comprises an acyl chain comprising from 12 to 30 carbon atoms.

17. The device of claim 16, wherein said polymeric substrate comprises a polyolefin, acrylic copolymer, polyamide, polyester, polyurethane, polycarbonate, polystyrene, fluorinated polymer, polyvinyl chloride, polyacrylonitrile, copolymers thereof, or mixtures thereof.

18. The device of claim 17, wherein the polymeric substrate comprises a polyolefin.

19. The device of claim 16, wherein said liquid membrane is stable for at least 30 days, 60 days or 90 days.

20. The device of claim 1, wherein the liquid membrane further comprises a nitroarylalkylether.

21. A device for performing liquid phase microextraction of at least one analyte from an aqueous sample comprising a liquid membrane supported on a porous polymeric substrate, wherein said liquid membrane has one side that can be placed in fluid communication with the aqueous sample containing the at least one analyte and a second side that can be placed in fluid communication with an acceptor solution, and wherein said liquid membrane comprises a fatty acid ester, or a vegetable oil, a silicone oil, or mixtures thereof, wherein the liquid membrane further comprises a preservative.

22. The device of claim 2, wherein the liquid membrane supported on a hollow fiber is stored in a closed container prior to use.

23. The device of claim 16, wherein the hollow fiber comprised of a porous polymeric substrate and a liquid membrane supported thereon is stored in a closed container prior to use.

24. The device of claim 16, wherein the liquid membrane further comprises a nitroarylalkylether.

25. A device for carrying out liquid phase microextraction of at least one analyte from an aqueous sample, said device comprising a hollow fiber comprised of a porous polymeric substrate and a liquid membrane supported thereon, wherein said liquid membrane comprises a fatty acid ester, or a vegetable oil, a silicone oil, or mixtures thereof, wherein the liquid membrane further comprises a preservative.

26. A device for carrying out liquid phase microextraction of at least one analyte from an aqueous sample, said device comprising a hollow fiber comprised of a porous polymeric substrate and a liquid membrane supported thereon, wherein said Liquid membrane comprises a mixture comprising a silicone oil and one or more of a fatty acid ester, a vegetable oil, or a nitroarylalkylether.

27. The device of claim 26, wherein the liquid membrane further comprises a carrier.

28. The device of claim 4, wherein the vegetable oil is soya oil, olive oil or tea tree oil.

29. The device of claim 16, wherein said liquid membrane further comprises a vegetable oil.

30. The device of claim 29, wherein the vegetable oil is soya oil, olive oil or tea tree oil.

* * * * *